(12) United States Patent
Segal et al.

(10) Patent No.: US 6,355,280 B1
(45) Date of Patent: Mar. 12, 2002

(54) COMPOSITION FOR REDUCING CELL APOPTOSIS CONTAINING AVOCADO AND SOYBEAN LIPID UNSAPONIFIABLES

(75) Inventors: Joseph Segal, 13 Greenbolm Street; Michael Schlosser, 51 Sheerit Hapleita Street, both of Haifa (IL), 34987; Ishak Neeman, Haifa (IL)

(73) Assignees: I.M.S. Cosmetics; Michael Schlosser; Joseph Segal, all of Haifa (IL)

( * ) Notice: Subject to any disclaimer, the term of this patent is extended or adjusted under 35 U.S.C. 154(b) by 0 days.

(21) Appl. No.: 09/514,595

(22) Filed: Feb. 28, 2000

(51) Int. Cl.$^7$ .................. A61K 35/78; A61K 9/14; A61K 9/20; A61K 9/06
(52) U.S. Cl. .................. 424/757; 424/725; 424/400; 424/401; 424/777
(58) Field of Search .................. 424/195.1, 725, 424/757, 401, 400, 777

(56) References Cited

U.S. PATENT DOCUMENTS

| | | | | |
|---|---|---|---|---|
| 4,608,392 A | * | 8/1986 | Jacquet et al. | 514/844 |
| 4,661,343 A | * | 4/1987 | Zabotto et al. | 424/59 |
| 4,847,072 A | * | 7/1989 | Bissett et al. | 424/59 |
| 5,045,565 A | * | 9/1991 | Gardner et al. | 514/487 |
| 5,165,915 A | * | 11/1992 | Tokubo et al. | 424/63 |
| 5,244,665 A | * | 9/1993 | Natraj et al. | 424/401 |
| 5,273,772 A | * | 12/1993 | Cooper | 426/611 |
| 5,468,490 A | | 11/1995 | Huber et al. | 424/78.03 |
| 5,698,199 A | * | 12/1997 | Mori et al. | 424/195.1 |
| 5,928,659 A | | 7/1999 | Moy | 424/401 |
| 5,948,451 A | * | 9/1999 | Igarashi | 426/2 |

FOREIGN PATENT DOCUMENTS

| | | | |
|---|---|---|---|
| BE | 886707 | | 9/1993 |
| EP | 180505 | | 10/1985 |
| FR | 4174 | | 8/1993 |
| WO | WO 98/05294 | * | 2/1998 |

OTHER PUBLICATIONS

Werman et al, "Partial Isolation and Characterization of a New Natural Inhibitor of Lysyl Oxidase from Avocado Seed Oil", *J. Agric. Food Chem.*, 38:2164–2168, 1990.

Rosenblat et al, "Chemical Characterization of Lysyl Oxidase Inhibitor from Avocado Seed Oil", *JAOCS*, 72(2): 225–229, 1995.

Kut et al, "Morphometric Analysis of Human Gingival Elastic Fibres Degradation by Human Leukocyte Elastase Protective Effect of Avocado and Soybean Unsaponifiables (ASU)", *Path. Biol.*, 46(7): 571–576, 1998 (Abstract only).

* cited by examiner

*Primary Examiner*—David M. Naff
*Assistant Examiner*—Mike Meller
(74) *Attorney, Agent, or Firm*—Mark M. Friedman

(57) ABSTRACT

A composition for reducing cell apoptosis is disclosed. The composition contains from about 0.01% to about 0.15% of a mixture of avacado lipid unsaponifiables and soybean lipid unsaponifiables which protects against the apoptotic effect of phorbol myristyl acetate (PMA). The composition also prevents the inhibition of cellular aging and for protection of the skin against negative environmental factors and pollutants.

19 Claims, 2 Drawing Sheets

COMPOSITION FOR REDUCING CELL APOPTOSIS CONTAINING AVOCADO AND SOYBEAN LIPID UNSAPONIFIABLES

FIELD AND BACKGROUND OF THE INVENTION

The present invention provides a preparation comprising an avocado and soybean unsaponifiable complex (ASU) for prevention of apoptosis, inhibition of cellular aging and for protection of the skin against negative environmental factors and pollutants.

Apoptosis, or programmed cell death is an evolutionary conserved mechanism essential for the development and maintenance of tissue homeostasis in multicellular organisms. Apoptosis results from the action of a genetically encoded suicide program that leads to a series of characteristic morphological and biochemical changes. These changes include activation of caspases, mitochondrial depolarization, cell volume loss, chromatin condensation and nucleosomal DNA defragmentation. It appears that the downstream biochemical events in apoptosis are the same regardless of the initial death stimulus [1].

A variety of key events in apoptosis focus on mitochondria, including the release of caspase activators (such as cytochrome c), changes in electron transport, loss of mitochondrial transmembrane potential, decrease of intracellular ATP concentration, altered cellular oxidation-reduction and participation of pro- and anti-apoptotic Bcl-2 family proteins [2].

Two major features of human aging clearly have been linked to alterations in the incidence of cell death, immunosenescence and neurodegeneration. In each of these case apoptosis plays a role in generation of these disorders. There is increasing evidence of the potential role of apoptosis in skin aging [3].

Apoptosis may be induced by various pathological conditions and a variety of agents, such as deprivation of tropic factors, heat shock and various cytotoxic substances [4] [5].

Skin is subjected daily to numerous negative environmental factors and pollutants. These pollutants include, but are not limited to atmospheric factors, chemical pollutants and biological pollutants. Examples of atmospheric factors that effect the skin include but are not limited to radiation such as Ultra-violet (UV) radiation from the sun, ozone, acid rain and extreme temperatures. Chemical and biological pollutants include pollutants from cars, industry, free radicals, cleaning materials, cosmetics, drugs and toxins. The background art discloses complex synthetic sun block preparations for protection against UV radiation. However, there are no effective preparations available for general protection of the skin against damage by environmental factors. In addition many of the sunblocks available have deleterious effects on the skin.

The vegetable oil unsaponifiables, such as avocado and soybean unsaponifiables are comprised of biologically active compounds, such as sterols, tocopherols, squalene and lipidic furans. These chemical groups exhibit a range of biological effects. Advantageous biological properties have been reported for avocado and soybean unsaponifiables. It was shown that a mixture of avocado and soybean unsaponifiables is beneficial in treatment of various disorders of connective tissue, such as wound healing and scleroderma. The background art contains several references of different cosmetic uses for ASU preparations.

U.S. Pat. No. 5,928,659 discloses a cosmetic composition comprising unsaponifiable lipids extracted from avocado for amelioration of skin keratoses that can be caused by aging of the skin and other skin lesions.

U.S. Pat. No. 5,468,490 discloses as supporting art that avocado preparations such as non-saponifiable fractions of avocado oil have useful dermatological properties for improving the appearance of aging, dry or wrinkled skin and for moisturizing and refreshing skin. It is further disclosed that lipid furans derived from avocado enhance the metabolism of skin, thereby improving its appearance. The enhanced metabolism results in increased elasticity and thickness of the skin and increased fibroblast population. These compounds are useful in combating dermal atrophy by slowing and even reversing thinning skin, wrinkles and other skin conditions, caused by chronological and photo aging of the skin.

EP Patent No. 180505 discloses cosmetic formulations containing avocado and soya unsaponifiables for retarding aging of the skin.

BE Patent No. 886707 discloses compositions containing avocado and soya unsaponifiables for use as cosmetics including skin creams.

FR Patent No. 4174 discloses compositions containing avocado and soya unsaponifiables for use in the treatment of conditions such as eczema.

The background art refers to several cosmetic uses of ASU. However, the background art does not does not teach or suggest uses of ASU preparations for protection against negative environmental factors, for inhibition of cellular aging, or prevention of apoptosis.

There is thus a widely recognized need for a natural derived preparation that can be used for general protection of the skin against negative environmental factors and pollutants, for inhibition of cellular aging and for prevention of apoptosis.

SUMMARY OF THE INVENTION

The present invention provides a preparation, preferably comprising an avocado and soybean unsaponifiable complex (ASU), for prevention of apoptosis. In addition the present invention provides a preparation for protection of the skin. In particular it concerns a preparation comprising avocado and soybean unsaponifiables for protection of the skin against negative environmental factors and pollutants. Moreover, the present invention provides a preparation comprising ASU which protects the skin from negative environmental factors and pollutants by stimulating ATP synthesis and preventing the breakdown of the mitochondrial membrane potential in the skin. Furthermore, the present invention provides a preparation, comprising an ASU complex for inhibition of cellular aging.

According to the teachings of the present invention there is provided in a first embodiment a composition for preventing cell apoptosis, comprising an effective amount of an avocado and soybean unsaponifiable component.

In a preferred embodiment the effective amount of an avocado and soybean unsaponifiable component is in a range of from about 1 μg/ml to about 10 μg/ml.

In a preferred embodiment the avocado and soybean unsaponifiable component is in a range of from about 1 μg/ml to about 5 μg/ml.

In a preferred embodiment the composition comprises from about 0.01% to about 0.15% of the avocado and soybean unsaponifiable component.

In a preferred embodiment the composition comprises from about 0.01% to about 0.05% of the avocado and soybean unsaponifiable component.

In a preferred embodiment the avocado and soybean unsaponifiable component is an avocado unsaponifiable.

In a preferred embodiment the avocado and soybean unsaponifiable component is a soybean unsaponifiable.

In a preferred embodiment the avocado and soybean unsaponifiable component is a lipidic furan derived from ASU.

In a preferred embodiment the avocado and soybean unsaponifiable component is a mixture of avocado unsaponifiables and soybean unsaponifiables.

In a preferred embodiment the avocado and soybean unsaponifiable component is a lipid furan.

In a preferred embodiment the composition further comprises one or a mixture of Ascorbyl Palmitate, fragrance, thickeners, herbal extracts, vitamins, dispersing agents, emulsifiers, binders, colorants, coenzyme-Q, anti-oxidants, natural vegetable oils and polyunsaturated fatty acids.

In a preferred embodiment the composition is administered orally.

In a preferred embodiment the composition is selected from the group consisting of powders or granules, suspensions, emulsions or solutions in water or non-aqueous media, oil or fat, sachets, capsules, tablets, gelcaps, food additives and sustained release formulations.

In a preferred embodiment the composition further comprises vitamins, anti-oxidants and a diluent.

In a preferred embodiment the composition further comprises vitamins, anti-oxidants and at least one oil.

In a preferred embodiment the composition is administered topically.

In a preferred embodiment the composition is in the form of a cream.

In a preferred embodiment the cream is a non-ionic oil-in water emulsion.

In a preferred embodiment the composition further comprises an oil phase and a water phase.

In a preferred embodiment the oil phase is selected form the group consisting of one of or a mixture of at least one oil, poly-unsaturated fatty acids, vitamins A, E and F, ascorbyl palmitate and anti-oxidants.

In a preferred embodiment the water phase is selected from the group consisting of water, plant extracts, humectants and non-ionic emulsifiers.

In a preferred embodiment the composition is in the form of lipophilic natural oil.

In a preferred embodiment the composition further comprises vegetable oils, polyunsaturated fatty acids, vitamins A, E and F, anti-oxidants and penetration enhancers.

In a preferred embodiment the penetration enhancers include propylene glycol di-pelargonate and ethoxydiaglycol.

In a preferred embodiment the vegetable oils include wheat germ oil, sesame oil, soybean oil, avocado oil, olive oil and rice oil.

In a preferred embodiment the polyunsaturated fatty acids include linoleic, linolenic acids-omega 3, gamma linolenic and arachidonic acid-omega 6.

In a second embodiment the present invention provides a composition for protection of the skin against pollutants, comprising an effective amount of an avocado and soybean unsaponifiable component.

In a preferred embodiment of the composition for protection of the skin against pollutants, the pollutant is selected from the group consisting of radiation, sun radiation, ozone, acid rain, extreme temperatures, transport pollutants, industry pollutants, cleaning materials, cosmetics, drugs, toxins and combinations thereof.

In a preferred embodiment of the composition for protection of the skin against pollutants, the avocado and soybean unsaponifiable component is in a range of from about 1 $\mu$g/ml to about 5 $\mu$g/ml.

In a preferred embodiment of the composition for protection of the skin against pollutants, the composition comprises from about 0.01% to about 0.05% of the avocado and soybean unsaponifiable component.

In a preferred embodiment of the composition for protection of the skin against pollutants, the avocado and soybean unsaponifiable component is an avocado unsaponifiable.

In a preferred embodiment of the composition for protection of the skin against pollutants, the avocado and soybean unsaponifiable component is a soybean unsaponifiable.

In a preferred embodiment of the composition for protection of the skin against pollutants, the avocado and soybean unsaponifiable component is a lipidic furan derived from ASU.

In a preferred embodiment of the composition for protection of the skin against pollutants, the avocado and soybean unsaponifiable component is a lipid furan.

In a preferred embodiment of the composition for protection of the skin against pollutants, the avocado and soybean unsaponifiable component is a mixture of avocado unsaponifiables and soybean unsaponifiables.

In a third embodiment the present invention provides a composition for preventing cell anti-aging, comprising an effective amount of avocado and soybean unsaponifiables.

In a preferred embodiment of the composition for preventing cell anti-aging the avocado and soybean unsaponifiable component is in a range of from about 1 $\mu$g/ml to about 5 $\mu$g/ml.

In a preferred embodiment of the composition for preventing cell anti-aging the composition comprises from about 0.01% to about 0.05% of the avocado and soybean unsaponifiable component.

In a preferred embodiment of the composition for preventing cell anti-aging the avocado and soybean unsaponifiable component is an avocado unsaponifiable.

In a preferred embodiment of the composition for preventing cell anti-aging the avocado and soybean unsaponifiable component is a soybean unsaponifiable.

In a preferred embodiment of the composition for preventing cell anti-aging the avocado and soybean unsaponifiable component is a lipidic furan derived from ASU.

In a preferred embodiment of the composition for preventing cell anti-aging the avocado and soybean unsaponifiable component is a mixture of avocado unsaponifiables and soybean unsaponifiables.

In a preferred embodiment of the composition for preventing cell anti-aging the composition is administered orally.

In a preferred embodiment of the composition for preventing cell anti-aging the composition is administered topically.

In a fourth embodiment the present invention provides a method of protecting the skin from damage, comprising the step of administering a composition of an avocado and soybean unsaponifiable component on skin cells.

In a preferred embodiment of the method of protecting the skin from damage the damage is damage from aging.

In a preferred embodiment of the method of protecting the skin from damage the damage is damage from pollutants.

In a preferred embodiment of the method of protecting the skin from damage the damage is damage from apoptosis.

The term 'apoptosis' as used herein refers to the process of cell death which results from an orderly pattern of morphological and biochemical changes.

The term 'negative environmental factors' as used herein refers to any substance in the water, atmosphere and environment that has deleterious effects on cells, especially skin cells, such as, but not limited to radiation such as UV radiation from the sun, ozone, acid rain and extreme temperatures, pollutants from cars, industry, free radicals, cleaning materials, cosmetics, drugs and toxins.

DESCRIPTION OF THE PREFERRED EMBODIMENTS

The present invention provides a preparation, preferably comprising an avocado and soybean unsaponifiable complex (ASU), for prevention of apoptosis. In addition the present invention provides a preparation for protection of the skin. In particular it concerns a preparation comprising avocado and soybean unsaponifiables for protection of the skin against negative environmental factors and pollutants. Moreover, the present invention provides a preparation comprising ASU which protects the skin from negative environmental factors and pollutants by stimulating ATP synthesis and preventing the breakdown of the mitochondrial membrane potential in the skin. Furthermore, the present invention provides a preparation, preferably a preparation comprising an ASU complex for inhibition of cellular aging.

Apoptosis may be induced by numerous pathological and physiological factors, such as cell aging and pollutants.

Skin is subjected daily to numerous negative environmental factors and pollutants. These pollutants include, but are not limited to atmospheric factors, chemical pollutants and biological pollutants. Examples of atmospheric factors that affect the skin include but are not limited to radiation such as UV radiation from the sun, ozone, acid rain and extreme temperatures. Chemical and biological pollutants include pollutants from cars, industry, free radicals, cleaning materials, cosmetics, drugs and toxins.

Pollutants cause the development of abnormal skin conditions, such as skin aging, skin irritation, dermatitis and low skin humidity. The general negative effect of such pollutants is changing the regulation of epidermal and dermal homeostasis resulting in cellular stress and the development of cellular apoptosis.

Different environmental pollutants or pathophysiological conditions interfere with the normal function of the mitochondria causing a perturbation of the transmembrane potential and generating superoxides by the uncoupled respiratory chain. Mitochondria are the primary system for ATP generation and therefore, toxic agents which interfere with their normal function would also affect the energy balance of the cells. The alterations of mitochondrial function is important in the cells apoptotic process and even in cell death. Without wishing to be limited by a single hypothesis the ASU complex inhibits apoptosis and thereby protects the skin by stimulating the ATP synthesis in the cells which stimulates energetic metabolism and ATP dependent reactions in disordered skin, preventing the breakdown of mitochondrial membrane potential. In this way the ASU complex protects cells, such as skin cells from apoptosis, cell aging and the negative effects of pollutants.

The composition of the present invention comprises an avocado unsaponifiable, a soybean unsaponifiable, a lipidic furan derived from ASU or a mixture thereof. Preferably, the composition of the present invention is a mixture of an avocado soybean unsaponifiable (ASU). The ASU composition is effective in an amount of from about 1 $\mu$g/ml to about 10 $\mu$g/ml and preferably from about 1 $\mu$g/ml to about 5 $\mu$g/ml. A formulation or composition containing the ASU composition contains from about 0.01% to about 0.15% (w/w) ASU and preferably from about 0.01% to about 0.05% (w/w) ASU. It has been shown that the ASU complex at these very low concentrations is very active. Surprisingly, at higher concentrations the ASU complex was found to cause cell damage and even cell death.

The composition of the present invention can optionally contain additional additives, such as Ascorbyl Palmitate, fragrance, thickeners, herbal extracts, vitamins, dispersing agents, emulsifiers, binders, colorants, coenzyme-Q, anti-oxidants, natural vegetable oils, polyunsaturated fatty acids or other suitable components. The polyunsaturated fatty acids are preferably, but not limited to linoleic, linolenic and arachidonic acid-omega 6. The composition of the present invention more preferably comprises the ASU complex, an essential fatty acid and an anti-oxidant.

The composition of the present invention can optionally be in various formulations depending on the route of administration. Optional routes of administration are preferably, but not limited to topical and oral.

Compositions for oral administration, can be in a form which includes powders or granules, suspensions, emulsions or solutions in water or non-aqueous media, oil or fat, sachets, capsules, tablets, gelcaps, food additives and sustained release formulations. A food additive containing the ASU complex can optionally be used as an additive to edible oils in foods, such as but not limited to bread, baking products, biscuits, crackers, dairy products, cakes, chocolate and food fats. Thickeners, diluents, flavorings, vitamins dispersing aids, emulsifiers or binders may be desirable. Preferred formulations for oral administration include gelatin capsules, preferably comprising ASU complex, vitamins, anti-oxidants and diluents (Example 9). An additional preferred formulation for oral administration comprises ASU complex, vitamins, anti-oxidants and edible oil (Example 10).

Suitable compositions for topical administration include, but are not limited to a gel, cream, mousse, lotion, oil, hydrophylic oil or other suitable formulation. Preferred compositions for topical administration include a cream or lipophilic natural oil. Preferably the cream composition is a non-ionic oil-in-water emulsion. A preferred cream composition for topical administration is a non-ionic oil-in-water emulsion. The non-ionic oil-in-water emulsion composition preferably comprises from about 30% to about 80% (w/w) oil phase, most preferably from about 35% to about 40% (w/w). The water phase is preferably in a range of from about 19% to about 70% (w/w) and most preferably from about 59% to about 65%. The concentration of the ASU complex is preferably from about 0.01% to about 0.15% (w/w) and most preferably from about 0.01% to about 0.05%. The oil phase is preferably comprised of at least one or a mixture of natural vegetable oils, polyunsaturated fatty acids, vitamins A, E and F, Ascorbyl Palmitate, anti-oxidants and other suitable components. The mixture of natural vegetable oils are preferably, but not limited to jojoba oil, avocado oil, soybean oil, sesame oil, rice oil, wheat germ oil, olive oil, sunflower oil, nut oil, cottonseed oil, coconut oil and corn oil or any other suitable natural vegetable oil.

The water phase of the cream composition is preferably comprised of a mixture of water, natural plant extracts, humectants, non-ionic emulsifiers and other suitable components. The cream can optionally be prepared by an inverse emulsion process by addition of a water phase to an oil phase.

The cream formulation can be optionally administered by topically applying onto the facial skin, neck, scalp, around the eyes and ton the body skin, preferably but not limited to twice daily. Application is especially preferable before exposure of the face and body skin to a hostile environment of toxins, pathogens, UV radiation, negative environmental factors and pollutants.

An additional preferred composition for topical administration is a lipophilic natural oil composition. The lipophilic natural oil composition preferably comprises a mixture of ASU complex, natural vegetable oils, polyunsaturated fatty acids, vitamins A, E and F, anti-oxidants, penetration enhancers and other suitable components. The ASU complex is preferably present in a concentration in the range of from about 0.01% to about 0.15% (w/w) and more preferably from about 0.01% to about 0.05% (w/w). The concentration of natural vegetable oils is preferably from about 20% to about 80% (w/w) and most preferably from about 65% to about 75% (w/w). The natural vegetable oils are preferably comprised of one or more of wheat germ oil, sesame oil, soybean oil, avocado oil, olive oil and rice oil. The fatty acids are preferably one or more of linoleic acid, linolenic acid, omega 3, gamma linolenic and arachidonic acid-omega 6 or mixtures thereof. The penetration enhancers are preferably present in a concentration of from about 0.5% to about 2.0% (w/w) and most preferably in a concentration of 2.0% (w/w). Preferred penetration enhancers include, but are not limited to propylene glycol dipelargonate and ethoxydiaglycol. The propylene glycol dipelargonate is preferably present in a concentration of about 1.60% (w/w) and ethoxydiaglycol is preferably present in a concentration of about 0.4% (w/w). Additional suitable components are optionally present in a range preferably from about 19% to about 80% (w/w).

The lipophilic natural oil composition can optionally be prepared by premixing the ASU complex in a part of the natural oils and addition of the premix to the remaining components of the preparation.

The lipophilic natural oil formulation can be optionally administered by topically applying onto the facial skin, neck, lips, scalp, around the eyes and on the body skin, preferably but not limited to twice daily. Application is especially preferable before exposure of the face and body skin to a hostile environment of toxins, pathogens, UV radiation, negative environmental factors and pollutants.

The ASU composition of the present invention has been shown to be effective in hamster and human cells. The ASU composition of the present invention minimized apoptosis resulting from exposure to toxins or calcium ionophores in human skin cells. Furthermore, ASU inhibited and protected fibroblast cells in hamsters from apoptosis.

It is to be understood that the invention is not limited in its application to the details of construction and the arrangement of the components set forth in the following description. The invention includes other embodiments and can be practiced or implemented in various ways. Also it is to be understood that the phraseology and terminology employed herein is for the purpose of description only and should not be regarded as limiting.

The present invention may be better understood with reference to the examples and the accompanying description.

EXAMPLE 1

The Protective Effect of ASU Preparation on Human Skin Against PMA Induced Apoptosis Human cultured foreskin fibroblasts were incubated with apoptosis induced stimuli, PMA (100 nM) for 15 min after cell pretreatment with ASU in a concentration range of 2–10 µg/ml for 1h (treatment group), or without cell pretreatment (negative control group). The mitochondria activity was measured by fluorescent Mito TrackerCMXRos incorporation into the mitochondria. CMXRos fluorescence is proportional to potential across the mitochondria membrane (transmembrane potential) and to absolute amount of Mito Tracker in mitochondria. The results are expressed in FIG. 1 as a percentage of the transmembrane potential of the positive control (non-treated) cells.

Figure 1:
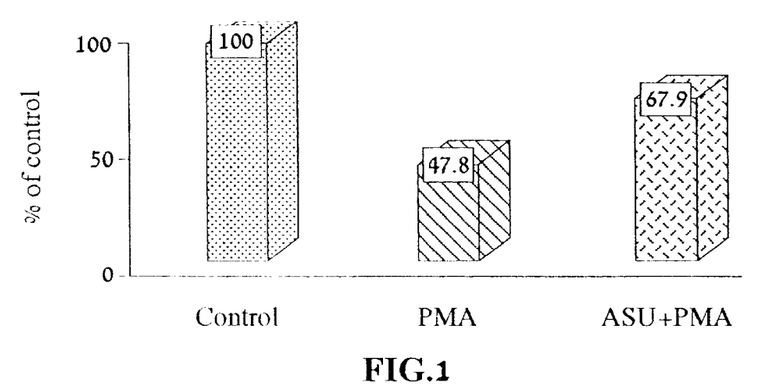
FIG. 1 shows the protective effect of ASU preparation on human skin fibroblast against PMA, which induces apoptosis.

From FIG. 1 it can be seen the CMXRos fluorescence was higher in the group pretreated with ASU, compared to the negative control group only incubated with PMA. There was thus a higher transmembrane potential in ASU pretreated cells. Pretreatment with the ASU complex minimized the negative effect of PMA.

EXAMPLE 2

A Further Experiment of the Protective Effect of ASU Preparation on Human Skin Against the Apoptosis Induced Stimuli PMA Human cultured foreskin fibroblasts were incubated with apoptosis induced stimuli, PMA (100 nM) for 15 min after cell pretreatment with ASU in a concentration range of 2–10 µg/ml for 1h (treatment group), or without cell pretreatment (negative control group). The apoptosis was detected by cell staining with fluorescent dye SYTO16. The apoptotic cells exhibit reduced fluorescence with SYTO16 [6]. The results are expressed in FIG. 2 as a percentage of the fluorescence of positive control (non-treated) cells.

Figure 2:
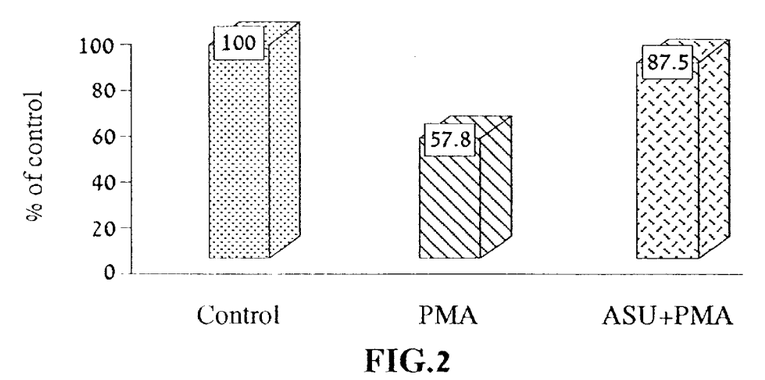
FIG. 2 shows the protective effect of ASU pretreatment on PMA-induced decrease of SYTO 16 fluorescence in cells.

From FIG. 2 it can be seen that pretreatment with the ASU complex, resulted in an increase in fluorescence compared to untreated cells incubated with PMA. There was thus less apoptosis in ASU pretreated cells. The ASU complex therefore minimized the negative effect of PMA.

EXAMPLE 3

Figure 3:
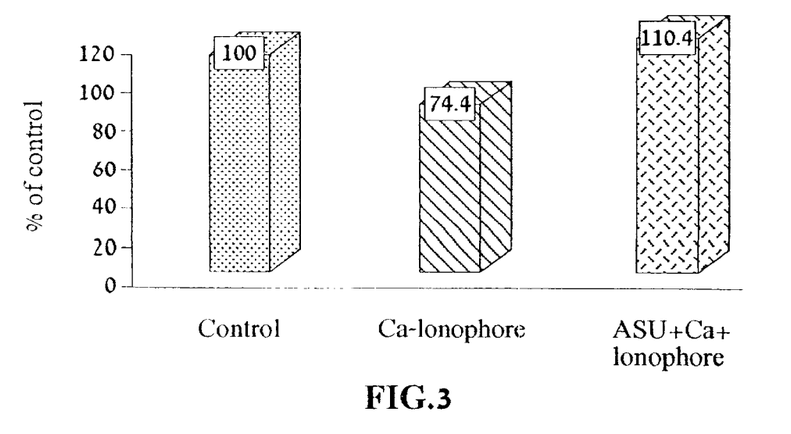
FIG. 3 shows the protective effect of ASU preparation on human skin fibroblasts against the apoptosis induced stimuli Ca-ionophore A 23187.

The Protective Effect of ASU Preparation Against the Apoptosis Induced Stimuli Calcium-ionophore A 23187 in Human Skin Fibroblasts Human cultured foreskin fibroblasts were incubated with apoptosis induced stimuli A 23187 ($Ca^{2+}$-ionophore) (10

NM) for 15 min either after cell pretreatment with ASU in a concentration range of 2–1 μg/ml for 1h (treatment group) or without pretreatment (negative control group). The apoptosis was detected by cell staining with fluorescent dye SYTO16. The results are shown in FIG. 3 and are expressed as percentage of fluorescence compared to the positive control (non-treated) cells.

From FIG. 3 it can be seen there was less fluorescence in the negative control group than in the ASU pretreated group. This indicates that pretreatment with ASU complex minimized the negative effect (apoptosis development) of the Ca-ionophore.

EXAMPLE 4

The Protective Effect of ASU Preparation Against Calcium-ionophore A 23187 and PMA Induced Decrease of Intracellular ATP Concentration in Hamster Fibroblasts.

Hamster BHK line fibroblasts were pretreated with ASU in a concentration range 2–10 μg/ml for 1h followed by treatment with $Ca^{2+}$-ionophore (10 μM) or PMA (100 nM) for 1h or without pretreatment (negative control group). The effect on the intracellular synthesis of ATP was measured by ATP bioluminescence (FIG. 4).

Figure 4:
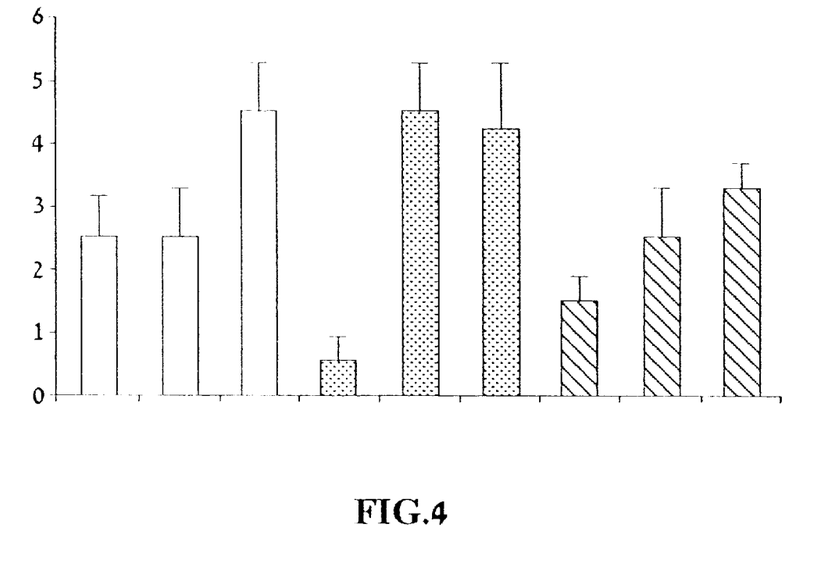
FIG. 4 shows the protective effect of ASU prepartion on hamster fibroblasts against Ca-ionophore A 23187 and phorbol myristyl acetate (PMA) induced decrease of intracellular ATP concentration.

From FIG. 4 it can be seen that there was augmentation of intracellular ATP concentration in the cells treated with 2 μg/ml ASU. In the cells incubated with $Ca^{2+}$-ionophore or PMA, there was an increase in ATP concentration with pretreatment with ASU 2 and 10 μg/ml. The effect was more notable when the lower concentration of 2 μg/ml ASU was used. It was therefore shown that cell pretreatment with ASU protected the cells against the decrease in ATP concentration caused by the apoptotic stimuli $Ca^{2+}$ ionophore and PMA.

EXAMPLE 5

The Protective Effect of ASU Preparation Against $Ca^{2+}$ Ionophore A 23187 and PMA Induced Decrease in DNA Synthesis in Hamster Fibroblasts Hamster BHK line fibroblasts were pretreated with ASU in a concentration range 2–10 μg/ml for 1 h followed by treatment with $Ca^{2+}$ ionophore (10 μM) (treatment group), or without treatment (negative control group). DNA synthesis was assayed after 4 h incubation of the cells with [$^3$H]-thymidine by monitoring [$^3$H]-thymidine incorporation into the acid insoluble fraction.

Figure 5:
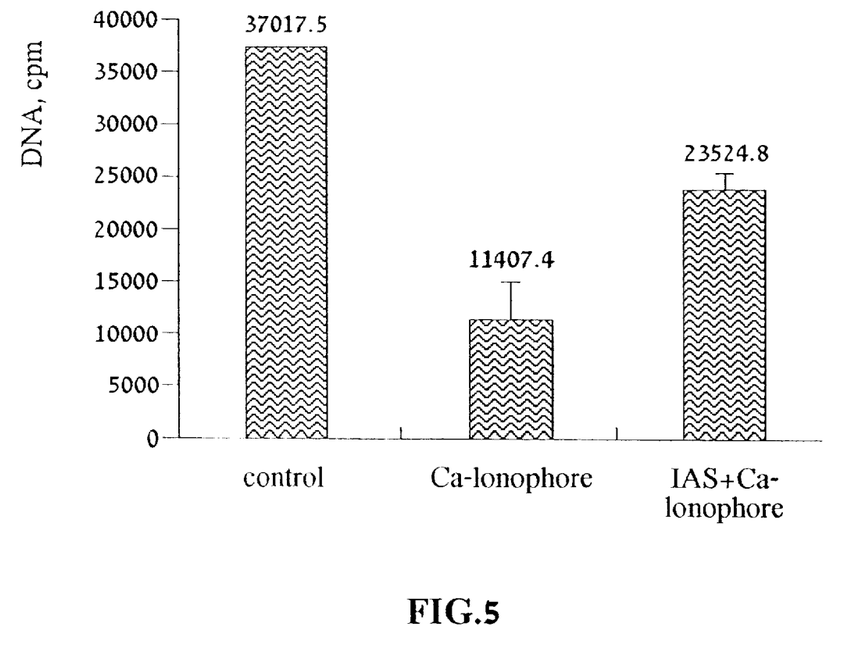
FIG. 5 shows the protective effect of ASU preparation on hamster fibroblasts against Calcium-ionophore A 23187 and PMA induced decrease in DNA synthesis.

The effect of ASU on DNA synthesis in cells treated with ASU and $Ca^{2+}$ ionophore can be seen in FIG. 5. It can be seen from FIG. 5 that there was higher DNA synthesis in the ASU pretreated fibroblasts than in the negative control. The ASU protected the cells from the $Ca^{2+}$ ionopohore A 23187 induced decrease in DNA synthesis.

EXAMPLE 6

Preparation of a Non-ionic Oil-In-Water Emulsion Cream Composition Containing ASU Complex for Topical Administration The non-ionic oil-in-water emulsion comprised 37% oil phase (w/w of the composition). The oil phase contained, wheat germ oil, polyunsaturated fatty acids, vitamins A, E and F, Ascorbyl Palmitate and anti-oxidants. The water phase was 62.99% (w/w) and contained a mixture of water, natural plant extracts, humectants and non-ionic emulsifiers. The concentration of the ASU complex was 0.01% (w/w).

The cream was prepared by an inverse emulsion process by addition of the water phase to the oil phase. The ASU complex was predissolved into the oil phase and the non-ionic emulsifiers were predissolved into the water phase. Both phases were preheated to 75° C. The emulsification was produced by a high speed homogenizer for 20 minutes, continued for another 60 minutes by a low-speed planetary mixer.

EXAMPLE 7

Preparation of a Lipophilic Natural Oil Composition Containing ASU Complex for Topical Administration The lipophilic natural oil composition comprised a mixture of ASU complex, jojoba oil, gamma linolenic acids, vitamins A, E and F, anti-oxidants and propylene glycol and dipelargonate ethoxydiaglycol. The ASU complex was present in a concentration of 0.05% (w/w). The concentration of natural vegetable oils was 70% (w/w). The propylene glycol dipelargonate was present in a concentration of about 1.60% (w/w) and ethoxydiaglycol was present in a concentration of about 0.4% (w/w). The additional components were present in a concentration of 27.95% (w/w).

The lipophilic natural oil composition was prepared by premixing the ASU complex in a part of the natural oils, followed by addition of the premix to the remaining components of the preparation.

EXAMPLE 8

General Method of Preparation of a Gelatin Capsule Containing ASU Complex for Oral Administration The gelatin capsule ASU formulation is made by premixing the components, the ASU complex, vitamins, anti-oxidants and diluents at a suitable temperature, depending on the components. Each gelatin capsule contains from about 200 mg to about 250 mg of this mixture.

EXAMPLE 9

A Gelatin Capsule ASU Composition for Oral Administration

The ASU composition was prepared by mixing the ASU complex and antioxidants in the amounts listed below at a temperature of about 40° C. The gelatin capsule contained about 0.250 g of this mixture.

| COMPONENT | AMOUNT % (w/w) |
| --- | --- |
| ASU complex | 0.01 |
| DL-α-Tocopherol | 0.02 |
| G-Palmitoyl-L-Ascorbic Acid | 0.01 |
| Diluent | 99.96 |

EXAMPLE 10

ASU Composition for Oral Administration

The ASU composition was prepared by premixing the ASU complex, and antioxidants in the amounts listed below in part of the oil at a temperature of about 40° C. This was followed by continued addition of the premix to the remaining oil.

The ASU composition for oral administration was also made replacing the soya oil with one or more of the following oils: corn oil, sunflower oil, avocado oil, sesame oil, cottonseed oil, wheat germ oil, peanut oil, palm oil, walnut oil, olive oil, coconut oil, cocoa butter and animal fat.

| COMPONENT | AMOUNT % (w/w) |
| --- | --- |
| ASU complex | 0.02 |
| DL-α-Tocopherol | 0.02 |
| G-Palmitoyl-L-Ascorbic Acid | 0.01 |
| Soya oil | 99.05 |

EXAMPLE 11

Method of Use of the ASU Composition of Example 7

The composition of Example 7 can be used without any other active ingredients. Optionally the ASU composition of Example 7 can be added to edible oils in different foods, such as but not limited to salads and salad dressings, mayonnaise, margarines, breads, confectionery, milk, meat, fish, or any vegetable substitute for animal protein.

EXAMPLE 12

Method of Use of ASU Complex for Protection of the Skin Against Pollutants

The ASU complex of the present invention can be used for protection of the skin against pollutants and for treatment of the skin for symptoms caused by exposure to pollutants. Examples of pollutants include, but are not limited to atmospheric factors, chemical pollutants and biological pollutants. Examples of atmospheric factors that effect the skin include but are not limited to radiation such as UV radiation from the sun, ozone, acid rain and extreme temperatures. Chemical and biological pollutants include pollutants from cars, industry, free radicals, cleaning materials, cosmetics, drugs and toxins. Exposure of a subject to pollutants can result in development of abnormal skin conditions, such as skin aging, skin irritation, dermatitis and low skin humidity.

The ASU complex of the present invention can be administered as a preventative measure or used for the therapeutic activity after exposure to any of the aforementioned pollutants.

Dosing is dependent on the responsiveness of the subject to the ASU complex. The ASU composition is effective in an amount of from about 1 $\mu$g/ml to about 10 $\mu$g/ml and preferably from about 1 $\mu$g/ml to about 5 $\mu$g/ml. A formulation containing the ASU composition preferably contains from about 0.01% to about 0.15% ASU and more preferably from about 0.01% to about 0.05% ASU. However higher or lower doses are possible. The dose and frequency of dosing would be dependent on the responsiveness of the subject. Persons of ordinary skill in the art can easily determine optimum dosages, dosing methodologies and repetition rates.

EXAMPLE 13

Method of Use of ASU Complex for General Anti-aging

The ASU complex of the present invention can be used for a general cell anti-aging effect.

The ASU complex of the present invention can be administered as a preventative measure in a young subject or used for the therapeutic activity after symptoms of aging are apparent. Preferred routes of administration of the ASU complex are oral and topical.

Dosing is dependent on the responsiveness of the subject to the ASU complex. The ASU composition is effective in an amount of from about 1 $\mu$g/ml to about 10 $\mu$g/ml and preferably from about 1 $\mu$g/ml to about 5 $\mu$g/ml. A formulation containing the ASU composition preferably contains from about 0.01% to about 0.15% ASU and more preferably from about 0.01% to about 0.05% ASU. However higher or lower doses are possible. The amount received by the subject is controlled. For example, the dose and frequency of dosing would be dependent on the responsiveness of the subject. Persons of ordinary skill in the art can easily determine optimum dosages, dosing methodologies and repetition rates

EXAMPLE 14

Method of Use of ASU for Prevention of Apoptosis

Apoptosis may be induced by numerous pathological and physiological factors, such as cell aging and pollutants.

The ASU complex of the present invention can be administered as a preventative measure or used for the therapeutic activity after exposure to any apoptosis inducing factor. For example, a subject exposed to pollution, may administer the ASU composition of the present invention to prevent apoptosis.

Dosing is dependent on the responsiveness of the subject to the ASU complex. The ASU composition is effective in an amount of from about 1 $\mu$g/ml to about 10 $\mu$g/ml and preferably from about 1 $\mu$g/ml to about 5 $\mu$g/ml. A formulation containing the ASU composition preferably contains from about 0.01% to about 0.15% ASU and more preferably from about 0.01% to about 0.05% ASU. However higher or lower doses are possible. The amount received by the subject is controlled. For example, the dose and frequency of dosing would be dependent on the responsiveness of the subject. Persons of ordinary skill in the art can easily determine optimum dosages, dosing methodologies and repetition rates.

EXAMPLE 15

Various Compositions of ASU

Topical and oral administration are the preferred routes of administration. Suitable compositions for topical administration include, but are not limited to a gel, cream, mousse, lotion, oil, hydrophylic oil or other suitable formulation. Preferred compositions for topical administration are a cream or lipophilic natural oil. The cream is preferably a non-ionic oil-in water emulsion.

Compositions for oral administration, can be in a form that include powders or granules, suspensions, emulsions or solutions in water or non-aqueous media, oil or fat, sachets, capsules, tablets, gelcaps, food additives and sustained release formulations. A food additive containing the ASU complex can optionally be used as an additive in edible oils in foods such as but not limited to bread, baking products, biscuits, crackers, dairy products, cakes, chocolate and food fats. Thickeners, diluents, flavorings, vitamins dispersing aids, emulsifiers or binders may be desirable.

A preferred composition for topical administration is a non-ionic oil-in-water emulsion. The non-ionic oil-in-water emulsion composition preferably comprises from about 30% to about 80% (w/w) oil phase, most preferably from about 35% to about 40% (w/w). The water phase is preferably in a range of from about 19% to about 70% (w/w) and most preferably from about 59% to about 65% (w/w). The concentration of the ASU complex is preferably from about 0.01% to about 0.15% (w/w) and most preferably from about 0.01% to about 0.05%. The oil phase is preferably comprised of at least one or a mixture of natural vegetable oils, polyunsaturated fatty acids, vitamins A, E and F, Ascorbyl Palmitate, anti-oxidants and other suitable components. The mixture of natural vegetable oils are preferably, but not limited to jojoba oil, avocado oil, soybean oil, sesame oil, rice oil, wheat germ oil or any other suitable natural vegetable oil. The water phase of the cream composition is preferably comprised of a mixture of water, natural plant extracts, humectants, non-ionic emulsifiers and other suitable components.

The cream formulation can be optionally administered by topically applying onto the facial skin, neck, scalp, around the eyes and ton the body skin, preferably but not limited to twice daily. Application is especially preferable before exposure of the face and body skin to a hostile environment of toxins, pathogens, UV radiation, negative environmental factors and pollutants.

The lipophilic natural oil composition preferably comprises a mixture of ASU complex, natural vegetable oils, polyunsaturated fatty acids, vitamins A, E and F, anti-oxidants, penetration enhancers and other suitable components. The ASU complex is preferably present in a concentration in the range of from about 0.01% to about 0.15% (w/w) and more preferably from about 0.01% to about 0.05% (w/w). The concentration of natural vegetable oils is preferably from about 20% to about 80% (w/w) and most preferably from about 65% to about 75% (w/w). The natural vegetable oils are preferably comprised of one or more of wheat germ oil, sesame oil, soybean oil, avocado oil, olive oil and rice oil. The fatty acids are preferably one or more of linoleic acid, linolenic acid, omega 3, gamma linolenic and arachidonic acid-omega 6 or mixtures thereof. The penetration enhancers are preferably present in a concentration of from about 0.5% to about 2.0% (w/w) and most preferably in a concentration of 2.0% (w/w). Preferred penetration enhancers include, but are not limited to propylene glycol dipelargonate and ethoxydiaglycol. The propylene glycol dipelargonate is preferably present in a concentration of about 1.60% (w/w) and ethoxydiaglycol is preferably present in a concentration of about 0.4% (w/w). Additional suitable components are optionally present in a range preferably from about 19% to about 80% (w/w).

The lipophilic natural oil formulation can be optionally administered by topically applying onto the facial skin, neck, lips, scalp, around the eyes and on the body skin, preferably but not limited to twice daily. Application is especially preferable before exposure of the face and body skin to a hostile environment of toxins, pathogens, UV radiation, negative environmental factors and pollutants.

Preferably, once the goal of treatment is achieved, treatment can be stopped until the signs and symptoms reappear.

It will be appreciated that the above examples and descriptions are intended only to serve as examples, and that many other embodiments are possible within the spirit and the scope of the present invention.

REFERENCES CITED

1. Heiden M G V., Chandel N S., Williamson E K., Schumacker P T., Thompsonm C B., Bcl-s regulates the membrane potential and volume homeostasis of mitochondria. Cell 91:627–637, 1997.
2. Green D R., Reed J. Mitochondria and apoptosis. Science 281: 1309–1312, 1998.
3. Haake A R., Roublevskaia I., Cooklis M. Apoptosis: a role in skin aging. J. Invest. Dermatol. Sympos. Proc. 3:28–35, 1998.
4. Fischer T C., Milner A E., Gredgory C D., Jackman A L., Wynne Ahernre C A., Hartley J A., Dive C., Hickman J A. Bel-2 modulation of apoptosis induced by anticancer drugs: resistance to thymidilate stress is independent of classical resistance pathway. Cancer Res. 53: 3321–3326, 1993.
5. Sahdstrom P A., Tobbey P W .m, Van Cleave S., Buttke T M. Lipid hydroperoxides induce apoptosis in T cells displaying HIV-associated Glutathione Peroxidase deficiency. J. Biol. Chem. 269: 798–801, 1994.
6. Poot M., Gibson L L., Singer V. L. Detection of apoptosis in live cells by MitoTrecker Red CMXRos and SYTO dye flow cytometry. Cytometry 27:358–364 (1997).

What is claimed is:

1. A composition for reducing cell apoptosis, comprising from about 0.01% to about 0.15% of a mixture of avocado lipid unsaponifiables and soybean lipid unsaponifiables which protects against the apoptotic effect of phorbol myristyl acetate (PMA).

2. The composition of claim 1, wherein said composition comprises from about 0.01% to about 0.05% of mixture.

3. The composition of claim 1, wherein said unsaponifiables comprise a lipidic furan.

4. The comprising of claim 1, further comprising one or a mixture of Ascorbyl Palmitate, fragrance, thickeners, herbal extracts, vitamins, dispersing agents, emulsifiers, binders, colorants, coenzyme-Q, anti-oxidants, natural vegetable oils and polyunsaturated fatty acids.

5. The composition of claim 1, wherein said composition is in a form for administering orally.

6. The composition of claim 5, wherein said composition is in a form selected from the group consisting of a powder; granules, a suspension, an emulsion, a solution in water, solution in a non-aqueous media, a capsule, a tablet, a gelcap, a food additive and a sustained release formulation.

7. The composition of claim 5, further comprising vitamins, anti-oxidants and a diluent.

8. The composition of claim 5, further comprising vitamins, anti-oxidants and at least one oil.

9. The composition of claim 1, wherein said composition is in a form for administering topically.

10. The composition of claim 9, wherein said composition is in the form of a cream.

11. The composition of claim 10, wherein said cream is a non-ionic oil-in water emulsion.

12. The composition of claim 11, further comprising an oil phase and a water phase.

13. The composition of claim 12, wherein said oil phase comprises a member selected from the group consisting of poly-unsaturated fatty acids, vitamins A, E and F, ascorbyl palmitate anti-oxidants, and mixtures thereof.

14. The composition of claim 12, wherein said water phase comprises a member selected from the group consisting of plant extracts, humectants and non-ionic emulsifiers.

15. The composition of claim 9, wherein said composition comprises a lipophilic natural oil.

16. The composition of claim 15, further comprising at least one item selected from the group consisting of a vegetable oil, a polyunsaturated fatty acid, vitamin A, vitamin E, vitamin F, an anti-oxidant and a penetration enhancer.

17. The composition of claim 16, wherein said penetration enhancers include propylene glycol di-pelargonate and ethoxydiaglycol.

18. The composition of claim 16, wherein said vegetable oil includes at least one item selected from the group consisting of wheat germ oil, sesame oil, soybean oil, avocado oil, olive oil and rice oil.

19. The composition of claim 16, wherein said polyunsaturated fatty acid includes at least one item selected from the group consisting of linoleic acid, linolenic acids-omega 3, gamma linolenic acid and arachidonic acid-omega 6.

* * * * *